United States Patent
Katou et al.

(10) Patent No.: US 8,287,842 B2
(45) Date of Patent: Oct. 16, 2012

(54) TOOTHPASTE COMPOSITION

(75) Inventors: Kazuhiko Katou, Sumida-ku (JP); Shigeto Kayane, Sumida-ku (JP)

(73) Assignee: Kao Corporation, Tokyo (JP)

( * ) Notice: Subject to any disclaimer, the term of this patent is extended or adjusted under 35 U.S.C. 154(b) by 1204 days.

(21) Appl. No.: 10/589,658

(22) PCT Filed: Mar. 4, 2005

(86) PCT No.: PCT/JP2005/003726
§ 371 (c)(1),
(2), (4) Date: Aug. 16, 2006

(87) PCT Pub. No.: WO2005/084624
PCT Pub. Date: Sep. 15, 2005

(65) Prior Publication Data
US 2007/0183991 A1    Aug. 9, 2007

(30) Foreign Application Priority Data
Mar. 5, 2004 (JP) ................................ 2004-061586

(51) Int. Cl.
*A61K 8/00* (2006.01)
*A61K 8/18* (2006.01)
*A61Q 11/00* (2006.01)

(52) U.S. Cl. ........................................................ 424/49
(58) Field of Classification Search ...................... 424/49
See application file for complete search history.

(56) References Cited

U.S. PATENT DOCUMENTS

| | | | |
|---|---|---|---|
| 5,234,274 A | 8/1993 | Honda et al. | |
| 5,702,686 A * | 12/1997 | Maekawa et al. | ................ 424/49 |
| 5,973,212 A * | 10/1999 | De Sadeleer et al. | ......... 568/852 |

FOREIGN PATENT DOCUMENTS

| | | |
|---|---|---|
| EP | 9325 | 4/1980 |
| EP | 0 966 952 | 12/1999 |
| JP | 7 238008 | 9/1995 |
| JP | 10 194926 | 7/1998 |
| JP | 2000-143468 | 5/2000 |
| JP | 2000 191483 | 7/2000 |
| JP | 2004 10485 | 1/2004 |
| JP | 2004-26816 | 1/2004 |
| WO | 00 56276 | 9/2000 |
| WO | 01/74323 | 10/2001 |

OTHER PUBLICATIONS

U.S. Appl. No. 11/512,326, filed Aug. 30, 2006, Kato.
Supplementary European Search Report issued Apr. 20, 2011 for European Patent Application No. 05 719 998.6.

* cited by examiner

*Primary Examiner* — Daniel Sullivan
*Assistant Examiner* — Rachael E Bredefeld
(74) *Attorney, Agent, or Firm* — Oblon, Spivak, McClelland, Maier & Neustadt, L.L.P.

(57) ABSTRACT

Provided is a toothpaste composition providing a pleasant cooling sensation and has excellent storage stability.
The toothpaste composition contains from 30 to 60 wt % of erythritol having an average particle size of 200 μm or less as Component (A), from 15 to 30 wt % of water as Component (B), and from 0.6 to 3 wt % of a binder as (C1).

12 Claims, No Drawings

TOOTHPASTE COMPOSITION

TECHNICAL FIELD

The present invention relates to a toothpaste composition excellent in a cooling sensation, feeling upon use and stability.

BACKGROUND OF THE INVENTION

Most of the purposes of brushing the teeth are to get a cooling sensation, as well as to clean the teeth. Flavorful cooling components contained in many toothpaste compositions, typically such as menthol, are essential for these purposes. In recent years, there has been a growing tendency toward more frequent eating of fatty foods or spices-containing foods, so that a toothpaste composition with more excellent cooling sensation is strongly desired.

As a method of heightening a cooling sensation, there are several methods known so far such that an amount of flavor components is increased or solvent components such as ethanol are added further. These methods, however, are so problematic that the intraoral stimulus becomes extremely strong or the foaming amount is suppressed adversely, thus leading to the deterioration of feeling upon use even after the teeth have been brushed with the composition.

A toothpaste composition excellent in a cooling sensation which contains an endothermic hydration reaction such as erythritol and having a water content adjusted to 10 wt. % or less is known (Patent Document 1).

[Patent Document 1] JP-A-2000-19148

DISCLOSURE OF THE INVENTION

In the present invention, there is thus provided a toothpaste composition containing the following components (A), (B) and (C1):
  (A) from 30 to 60 wt % of erythritol having an average particle size of 200 μm or less,
  (B) from 15 to 30 wt % of water, and
  (C1) from 0.6 to 3 wt % of a binder.

In another aspect of the present invention, there is also provided a toothpaste composition containing the following components (A), (B) and (C1):
  (A) from 25 to 60 wt % of erythritol having an average particle size of 200 μm or less,
  (B) from 15 to 30 wt % of water, and
  (C1) from 0.6 to 3 wt % of a binder.

In a further aspect of the present invention, there is also provided a toothpaste composition containing the following components (A), (B) and (C2):
  (A) from 30 to 60 wt % of erythritol having an average particle size of 200 μm or less,
  (B) from 15 to 30 wt % of water, and
  (C2) from 0.6 to 3 wt % of at least two binders selected from the group consisting of sodium alginate, sodium carboxymethylcellulose, carrageenan, xanthan gum, sodium polyacrylate, hydroxyethyl cellulose, hydroxypropyl cellulose, pectin, tragacanth gum, arabic gum, guar gum, karaya gum, locust bean gum, gellan gum, tamarind gum, Psyllium seed gum, polyvinyl alcohol, sodium chondroitin sulfate, and methoxyethylene-maleic anhydride copolymer.

MODE FOR CARRYING OUT THE INVENTION

It has been elucidated that when the toothpaste composition as described in Patent Document 1 is stored for a long period of time, it separates water or another liquid component therefrom. The present inventors therefore increased an amount of a binder in order to improve the storage stability of the toothpaste composition. The toothpaste composition had a water content of 10 wt. % or less and the amount of water was not enough for dissolving the binder therein. As a result, an increase in the amount of a binder was not effective for preparing a uniform and stable toothpaste composition. As another measure, the water content was increased in order to overcome this problem, but an increase in the water content deteriorated a cooling sensation induced by a sugar alcohol such as erythritol. It was therefore difficult to prepare a toothpaste composition having both stability and pleasant cooling sensation. As a result of further investigation, it has been found that even if a sufficient amount of water is added in order to dissolve a binder therein, intraoral diffusion and melting of erythritol can be controlled and a sufficient cooling sensation can be provided by incorporating erythritol having a specific particle size and adjusting the amounts of the binder and erythritol. It has also been found that the feeling upon use is improved further by using two or more specific binders in combination.

According to the present invention, a toothpaste composition featuring an excellent cooling sensation and long-term stability can be provided. In addition, a toothpaste composition containing a specific binder, which has good shape retention, less threading property and good feeling upon use can be provided.

Erythritol (Component A) has three isomers, that is, L-erythritol, D-erythritol and meso-erythritol. Any one of these isomers may be used in the present invention. As the erythritol to be used in the present invention, that prepared by fermentation of glucose is preferred. Examples of such erythritol include those manufactured by Nikken Chemicals, Co., Ltd., Mitsubishi-Kagaku Foods Corporation and Cerestar Holding BV.

In the present invention, erythritol having an average particle size of 200 μm or less is employed because it can provide a more pleasant cooling sensation and does not cause a strange feeling in the oral cavity. The average particle size is preferably from 30 to 200 μm, more preferably from 30 to 150 μm, still more preferably from 30 to 100 μm. Such erythritol having an average particle size of 200 μm or less can be prepared by grinding crystalline erythritol.

The average particle size can be measured in the following manner.

Sieve: JIS standard sieve having φ75 mm.
Screen size: Below a stack of sieves having screen sizes, in the descending order, of 500 μm, 355 μm, 250 μm, 180 μm, 125 μm, 90 μm and 45 μm, a receptor is placed.
Agitator: Micro Electromagnetic Vibrating Feeder M-2 (Tsutsui Rikagaku Kikai Co., Ltd.)
Method: A sample (15 g) is placed on a 500-μm sieve and classified for 5 minutes by an electromagnetic vibrating feeder. A minus sieve ratio (cumulative amount) is plotted on normal probability paper and a particle size corresponding to 50% is designated as an average particle size.

The content of erythritol having an average particle size of 200 μm or less in the toothpaste composition of the present invention is necessarily from 25 to 60 wt %, preferably from 30 to 60 wt %, more preferably from 35 to 55 wt %, still more preferably from 38 to 50 wt % from the viewpoint of attaining the storage stability and a higher cooling sensation. When the erythritol content is less than 25 wt %, a sufficient cooling sensation cannot be accomplished, while when the erythritol content exceeds 60 wt %, the proportion of powder components in the composition becomes unduly high, leading to a problem that the composition gradually hardens after preparation. In addition, the cost of the composition becomes high. It is therefore preferred to adjust the erythritol content in the composition not greater than 60 wt %. Erythritol having an average particle size of 200 µm or less is added to the composition preferably in an amount of from 30 to 60 wt %, more preferably from 35 to 60 wt %, still more preferably from 35 to 55 wt %, especially preferably from 35 to 50 wt %.

The water content (Component (B)) in the toothpaste composition of the present invention is necessarily from 15 to 30 wt %, more preferably from 15 to 25 wt % from the viewpoint of accomplishing the storage stability and a high cooling sensation. When the water content is less than 15 wt %, the composition has reduced stability because the binder cannot be dissolved completely in water. When the water content exceeds 30 wt %, a dissolution amount of erythritol increases, making it difficult to attain a sufficient cooling sensation.

No particular limitation is imposed on the binder (Component (C1)) to be used in the present invention, but at least two binders (C2) selected from the group consisting of sodium alginate, sodium carboxymethylcellulose, carrageenan, xanthan gum, sodium polyacrylate, hydroxyethyl cellulose, hydroxypropyl cellulose, pectin, tragacanth gum, arabic gum, guar gum, karaya gum, locust bean gum, gellan gum, tamarind gum, Psyllium seed gum, polyvinyl alcohol, sodium chondroitin sulfate, and methoxyethylene-maleic anhydride copolymer are preferred. Use of any two of theses binders is preferred from the viewpoints of shape retention of the toothpaste composition and prevention of a threading property. Use of at least three of the above-described binders in combination is more preferred.

Of the above-described binders, as sodium alginate, that having an intramolecular mannuronic acid/guluronic acid ratio (M/G ratio) of from 0.5 to 2.5 and easily commercially available from KIMICA, Dainippon Pharmaceutical or the like is preferred. As sodium carboxymethylcellulose, that having a degree of etherification of from 0.6 to 2.5, more preferably from 0.8 to 1.5 and easily commercially available from Daicel Chemical Industries, Daiichi Kogyo Seiyaku or the like is preferred. As carrageenan, any one of three isomers, that is, kappa, lambda and iota may be used. They are commercially available from CP Kelco, MRC Polysaccharide, Taiyo Kagaku, or the like. Those easily available can be used, but iota carrageenan and lambda carrageenan are more preferred. Xanthan gum is commercially available from Taiyo Kagaku, CP Kelco and Dainippon Pharmaceutical. Those easily available can be used. When xanthan gum is used in combination with carboxymethyl cellulose, xanthan gum having low cellulase activity, that is, xanthan gum from which a small amount of cellulase contained therein has been removed is preferably used.

Of these binders, use of at least two, especially at least three binders selected from sodium alginate, sodium carboxymethylcellulose, carrageenan, xanthan gum, sodium polyacrylate, hydroxyethyl cellulose, hydroxypropyl cellulose, tragacanth gum, arabic gum, karaya gum, gellan gum, tamarind gum, and methoxyethylene-maleic anhydride copolymer in combination is preferred. Use of two or more binders selected from sodium alginate, sodium carboxymethylcellulose, carrageenan and xanthan gum is more preferred.

The content of the binder (C1) in the toothpaste composition of the present invention is necessarily from 0.6 to 3 wt %, preferably from 0.8 to 2.5 wt %, more preferably from 1.0 to 2 wt % from the viewpoints of stability and shape retention, and feeling upon use such as threading property. The composition having a binder content less than 0.6 wt % is inferior in stability and feeling upon use, while the composition having a binder content exceeding 3 wt % has an unduly high viscosity, which prevents uniform spreading of the composition, smooth release of flavor components and provision of a cooling sensation.

The amounts of the above-described components (A), (B) and (C1) in the toothpaste composition of the present invention preferably fall within a range of the following equation (1):

$$(B) \times 0.3 + 25 \leq (A) \quad (1)$$

from the standpoint of improvement in a cooling sensation. More preferably, they fall within a range of the following equation (2):

$$(B) \times 0.3 + 30 \leq (A) \quad (2)$$

The coefficient 0.3 of (B) in the formulas (1) and (2) is determined based on the fact that the solubility (5° C.) of erythritol in 100 g of water is 30 g. The section 25 or 30 is a preferable amount of erythritol to be incorporated in a non-water-based toothpaste composition in view of allowing the composition to exhibit a cooling sensation, in other words, the preferable minimum amount (%) of erythritol which remains in the toothpaste composition as a powder.

In addition, they preferably fall within a range of the following equation (3):

$$(C1) \times 10 \leq (B) \quad (3)$$

from the viewpoints of stability, shape retention and threading property.

The toothpaste composition of the present invention may contain, in addition to the above-described components, for example, a foaming agent, a foaming assistant, an abrasive, a humectant, a sweetener, a preservative, an enzyme, a pH regulator, a bactericide, a medicinal component, a pigment, a colorant and flavor as needed.

Examples of the abrasive preferably used in the invention include silica abrasives such as precipitated silica, silica gel, aluminosilicate and zirconosilicate, secondary calcium phosphate dihydrate or anhydrate, calcium pyrophosphate, calcium carbonate, alumina, aluminum hydroxide, magnesium acetate, tertiary magnesium phosphate, zeolite and synthetic resin abrasives.

Preferred examples of the humectant include glycerin, sorbitol, propylene glycol, polyethylene glycol, xylitol, maltitol, lactitol and trehalose.

Examples of the sweetener include saccharin sodium, aspartame, sucralose, thaumatin, acesulfame potassium, stevioside, stevia extract, paramethoxy cinnamic aldehyde, neohesperidyl dihydrochalcone and perillartine.

Examples of the flavor include 1-menthol, carvone, anethole, eugenol, limonene, peppermint oil, spearmint oil, ocimene, n-amyl alcohol, citronellol, α-terpineol, methyl salicylate, methyl acetate, citronellol acetate, cineol, linalool, ethyl linalool, vanillin, thymol, lemon oil, orange oil, sage oil, rosemary oil, cinnamon oil, pimento oil, perilla oil, clove oil and eucalyptus oil.

Examples of the other various effective ingredients include water-soluble phosphoric acid compounds such as potassium salt or sodium salt of orthophosphoric acid, allantoin chlorohydroxyaluminum, hinokitiol, lysozyme chloride, glycyrrhizinic acid and salts thereof, sodium chloride, tranexamic acid, epsilon-aminocaproic acid, dl-tocopherol acetate, azulene, glycyrrhetinic acid, copper compounds such as sodium copper chlorophyllin and copper gluconate, aluminum lactate, strontium chloride, potassium nitrate, berberine, hydroxamic acid and derivatives thereof, sodium tripolyphosphate, zeolite, dextranase, mutanase, amylase, methoxyethylene, maleic anhydride copolymer, polyvinylpyrrolidone, epidihydrocholesterin, dihydrocholesterol, zinc citrate, extracts of Japanese angelica roots, phellodendron barks, clove, rosemary, scutellaria roots, safflower, and the like, α-bisabolol, chlorhexidine salts, triclosan, cetylpyridinium chloride, benzethonium chloride, and trichlorocarbanilide.

In the toothpaste composition of the present invention, erythritol is dispersed desirably as a powder in the composition from the standpoint of exhibition of a sufficient cooling sensation. Erythritol is therefore added in the powder form in the final stage of the preparation of the composition. Since such a preparation process is employed, erythritol sparingly dissolves in water and can exist in the powder form in the toothpaste composition. Described specifically, the toothpaste composition of the present invention can be prepared by weighing the formulation amount of each component such as a purified water, a humectant, a binder, a flavor, a preservative, a abrasive, a foaming agent, a sweetener and a medicinal component, mixing them in accordance with specific preparation conditions, swell the binder sufficiently, add an abrasive, a foaming agent, a flavor and erythritol in the powder form further, and mixing them while defoaming.

The toothpaste composition of the present invention has a viscosity at 25° C. (Helipath viscometer, rotor C, 2.5 rpm, 1 minute) of preferably from 1500 to 5000 dPa·s, more preferably from 2000 to 4500 dPa·s, especially preferably from 2500 to 4000 dPa·s.

EXAMPLES (1) Preparation of Toothpaste Composition

Toothpastes of Examples 1 to 4 and Comparative Examples 1 to 3 were prepared in accordance with the compositions as shown in Table 1. Erythritol was added in the final stage of the preparation process.

(2) Evaluation of Cooling Sensation

Ten volunteers (five males and five females) put 1 g of each toothpaste on their toothbrush and brush their teeth for about 2 minutes freely. Using the toothpaste of Comparative Example 3 as a reference toothpaste, they evaluated, as a cooling sensation, the degree of a refreshed feeling in the mouth after rinsing the mouth with water based on the below-described criteria.

Evaluation Criteria of the Cooling Sensation
 A: Obviously superior in refreshed feeling to the reference toothpaste
 B: A little superior in refreshed feeling to the reference toothpaste
 C: Comparable in refreshed feeling to the reference toothpaste The numeral shown as the judgment result in Table is that of the most common evaluation among 10 volunteers.

(3) Evaluation of the Storage Stability

The toothpastes as shown in Table 1 were each filled in a toothpaste tube for storage and stored for 3 months at each of 5° C., room temperature and 40° C. The tube was then cut through and whether the liquid component was separated from the toothpaste or not was evaluated based on the following criteria.

Evaluation Criteria of Storage Stability
 A: Separation of a liquid component is not observed at all.
 B: Separation of a liquid component is observed slightly.
 C: Separation of a liquid component is observed obviously.

(4) Evaluation of Shape Retention

Each toothpaste was squeezed out from the tube and put on the entirety of a toothbrush and the state of the toothpaste after it was allowed to stand for 10 seconds was evaluated based on the below-described criteria.

Evaluation Criteria of Shape Retention
 A: Shape just after the toothpaste is squeezed out on the toothbrush is maintained.
 B: Shape just after the toothpaste is squeezed out on the toothbrush is almost maintained.
 C: The toothpaste sags from the toothbrush and cannot maintain its shape.

(5) Evaluation of Threading Property

The threading property of each toothpaste when it was squeezed out on the entirety of a toothbrush and slowly pulled up was evaluated based on the below-described criteria.

Evaluation Criteria of Threading Property
 A: The toothpaste can be put on a toothbrush smoothly without threading.
 B: The toothpaste can be put on a toothbrush smoothly, though it causes slight threading.
 C: The toothpaste cannot be put on a toothbrush smoothly because of severe threading.

TABLE 1

| Components (mass %) | Examples | | | | Comparative Examples | | |
|---|---|---|---|---|---|---|---|
| | 1 | 2 | 3 | 4 | 1 | 2 | 3 |
| Erythritol (average particle size: 80 μm) | 40 | 50 | 60 | | 40 | 40 | |
| Erythritol (average particle size: 200 μm) | | | | 40 | | | |
| Purified water | 20 | 25 | 18 | 20 | 5 | 20 | 20 |
| Sodium alginate | 0.5 | 0.3 | | 0.4 | | | |
| sodium Carboxymethycellulose | 1 | 0.8 | 0.8 | 1.2 | 1 | | |
| Carrageenan | | 0.4 | 0.6 | | | | |
| Xanthan gum | 0.05 | | | 0.05 | 0.2 | 0.5 | 0.5 |
| Sodium fluoride | 0.21 | 0.21 | | 0.21 | | | |
| Sodium monofluorophosphate | | | 0.7 | | | | |
| Sorbitol | q.s. | | | q.s. | | | q.s. |
| Xylitol | | | q.s. | | | | |
| Glycerin | | q.s. | | | 20 | 16.2 | 40 |
| Polyethylene glycol (PEG6000) | 5 | | 5 | 5 | | | 5 |
| Propylene glycol | | 5 | | | 30.5 | 20 | |
| Saccharin sodium | 0.05 | 0.05 | 0.02 | 0.05 | 0.1 | | 0.05 |
| Abrasive silica | 10 | 10 | 5 | 10 | 5 | 2 | 10 |
| Sodium lauryl sulfate | 1.5 | 1.5 | 1.5 | 1.5 | 1.5 | 1.5 | 1.5 |
| Triclosan | | 0.1 | | | | | |
| Benzethonium chloride | | | 0.01 | | | | |
| dl-α-Tocopherol hydrochloride | | 0.1 | | | | | |
| β-Glycyrrhetinic acid | 0.01 | | | | | | |

TABLE 1-continued

|  | Components (mass %) | Examples | | | | Comparative Examples | | |
| --- | --- | --- | --- | --- | --- | --- | --- | --- |
|  |  | 1 | 2 | 3 | 4 | 1 | 2 | 3 |
| Flavor | | 1.2 | 1.2 | 1.2 | 1.2 | 1.2 | 1.2 | 1.2 |
| Total | | 100 | 100 | 100 | 100 | 100 | 100 | 100 |
| Cooling sensation | | A | A | A | B | A | C | Reference |
| Storage stability | 3 months at 5° C. | A | A | A | A | C | B | A |
|  | 3 months at room temperature | A | A | A | A | C | B | A |
|  | 3 months at 40° C. | A | A | B | A | C | B | B |
| Shape retention | | A | A | A | A | A | C | B |
| Threading property | | A | A | A | A | A | C | C |

As is shown in Table 1, the toothpastes obtained in Examples 1 to 3 contain a high concentration of erythritol, an adequate amount of water, and in addition, at least two appropriate binders so that they feature a strong cooling sensation and good storage stability and moreover, exhibit good shape retention and threading preventive effect. The toothpaste obtained in Example 4 contains erythritol having an average particle size of 200 μm so that compared with those obtained in Examples 1 to 3, it is a little inferior in cooling sensation. This suggests that when erythritol has an average particle size exceeding 200 μm, the toothpaste containing it does not produce a sufficient cooling sensation.

The toothpaste obtained in Comparative Example 1, on the other hand, produces a good cooling sensation, but owing to an insufficient water content, it is inferior in the storage stability. The toothpaste obtained in Comparative Example 2 does not contain a sufficient amount of a binder so that it does not provide a satisfactory cooling sensation. In addition, its shape retention and threading property are not sufficient because it contains only one binder.

The invention claimed is:

1. A toothpaste composition comprising:
   (A) from 30 to 60 wt % of erythritol having an average particle size of 200 μm or less,
   (B) from 15 to 30 wt % of water, and
   (C1) from 0.6 to 3 wt % of a binder,
   wherein equation (1) is satisfied:

$$(\text{wt \% of } (B) \text{ water}) \times 0.3 + 25 \leq (\text{wt \% of } (A) \text{ erythritol}) \quad (1).$$

2. A toothpaste composition comprising:
   (A) from 30 to 60 wt % of erythritol having an average particle size of 200 μm or less,
   (B) from 15 to 30 wt % of water, and
   (C2) from 0.6 to 3 wt % of at least two binders selected from the group consisting of sodium alginate, sodium carboxymethylcellulose, carrageenan, xanthan gum, sodium polyacrylate, hydroxyethyl cellulose, hydroxypropyl cellulose, pectin, tragacanth gum, arabic gum, guar gum, karaya gum, locust bean gum, gellan gum, tamarind gum, Psyllium seed gum, polyvinyl alcohol, sodium chondroitin sulfate, and methoxyethylene maleic anhydride copolymer,
   wherein equation (1) is satisfied:

$$(\text{wt \% of } (B) \text{ water}) \times 0.3 + 25 \leq (\text{wt \% of } (A) \text{ erythritol}) \quad (1).$$

3. The toothpaste composition according to claim 2, wherein (C2) comprises at least two binders selected from the group consisting of sodium alginate, carboxymethylcellulose sodium, carrageenan and xanthan gum.

4. The toothpaste composition according to claim 2, wherein (C2) comprises at least three binders selected from the group consisting of sodium alginate, sodium carboxymethylcellulose, carrageenan, xanthan gum, sodium polyacrylate, hydroxyethyl cellulose, hydroxypropyl cellulose, pectin, tragacanth gum, gum arabic, guar gum, karaya gum, locust bean gum, gellan gum, tamarind gum, Psyllium seed gum, polyvinyl alcohol, sodium chondroitin sulfate, and methoxyethylene maleic anhydride copolymer.

5. The toothpaste composition according to claim 1, wherein the composition has a viscosity at 25° C. of from 1500 to 5000 dPa·s.

6. The toothpaste composition according to claim 2, wherein the composition has a viscosity at 25° C. of from 1500 to 5000 dPa·s.

7. The toothpaste composition according to claim 1, wherein (C1) comprises at least one binder selected from the group consisting of sodium alginate, sodium carboxymethylcellulose, carrageenan, xanthan gum, sodium polyacrylate, hydroxyethyl cellulose, hydroxypropyl cellulose, pectin, tragacanth gum, arabic gum, guar gum, karaya gum, locust bean gum, gellan gum, tamarind gum, Psyllium seed gum, polyvinyl alcohol, sodium chondroitin sulfate, and methoxyethylene maleic anhydride copolymer.

8. The toothpaste composition according to claim 1, wherein the erythritol (A) is obtained by grinding crystalline erythritol.

9. The toothpaste composition according to claim 1 that provides a superior cooling sensation when used by a subject compared to an otherwise similar toothpaste that does not contain erythritol.

10. The toothpaste composition according to claim 1 that is stable for 3 months when stored at 4° C., room temperature or 40° C.

11. The toothpaste composition according to claim 1 that retains its shape when expressed from a tube and placed on the end of a toothbrush.

12. The toothpaste composition according to claim 1 that is applicable on a toothbrush smoothly without threading.

* * * * *